United States Patent [19]
Murai et al.

[11] 4,103,009
[45] Jul. 25, 1978

[54] BENZOGUANAMINE DERIVATIVES

[75] Inventors: Hiromu Murai, Otsu; Katsuya Ohata, Uji; Yoshiaki Aoyagi, Kyoto; Fusao Ueda, Shiga; Masahiko Kitano, Kyoto; Shinichi Tada, Joyo, all of Japan

[73] Assignee: Nippon Shinyaku Co., Ltd., Japan

[21] Appl. No.: 768,091

[22] Filed: Feb. 14, 1977

[30] Foreign Application Priority Data

Mar. 29, 1976 [JP] Japan ................................. 51-34948

[51] Int. Cl.$^2$ .................... C07D 251/48; A61K 31/53
[52] U.S. Cl. .................................... 424/249; 544/206

[58] Field of Search ..................... 260/249.9; 544/206; 424/249

[56] References Cited
U.S. PATENT DOCUMENTS 3,966,728  6/1976  Murai et al. ........................ 260/249.9

*Primary Examiner*—John M. Ford
*Attorney, Agent, or Firm*—Jacobs & Jacobs

[57] ABSTRACT

2,4-Diamino-6-phenyl-s-triazine derivatives which are substituted in the 3-position of the phenyl ring and optionally further substituted in the 6-position demonstrate anti-ulcer and diuretic properties. A representative embodiment is 2,4-diamino-6-(3-trifluoromethylthiophenyl)-s-triazine.

14 Claims, No Drawings

BENZOGUANAMINE DERIVATIVES

DETAILED DESCRIPTION

The present invention pertains to compounds selected from the group consisting of benzoguanamine derivatives represented by the formula:

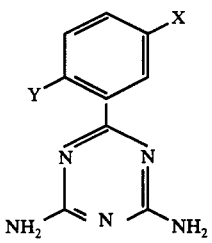

wherein
X is halo, lower alkylthio, lower alkylsulfonyl, sulfamyl, N,N-di(lower alkyl)sulfamyl, trifluoromethyl or trifluoromethylthio; and
Y is hydrogen, halogeno, lower alkoxy or lower alkoxy(lower alkoxy), and
the pharmaceutically acceptable acid addition salts thereof.

In a first embodiment the invention pertains to compounds of the above formula wherein X is chloro, bromo, methylthio, methylsulfonyl, sulfamyl, dimethylsulfamyl, trifluoromethyl or trifluoromethylthio.

In a further embodiment the invention pertains to compounds wherein Y is hydrogen, chloro, methoxy or methoxyethoxy.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term halo denotes the monovalent substituents fluoro, chloro, bromo and iodo.

The compounds of the present invention demonstrate antiulcergenic and diuretic properties. In connection with the first of these activities, the compounds can be used either prophylactically or therapeutically in the treatment of gastric ulcers. The compounds can also be utilized to effect diuresis, as is desirable for example in hypertension.

The compounds can be produced by a variety of chemical methods.

In a first embodiment, an appropriately substitued benzonitrile is allowed to react with a dicyanodiamide. Alternatively, a substituted benzoic acid derivative such as a lower alkyl ester is allowed to react with a biguanide. These reactions are conducted in a conventional manner as has been used heretofore in the synthesis of other benzoguanamine derivatives. Sulfamyl substituents can also be introduced from the corresponding benzoguanamine through direct replacement reactions and, in accordance with known techniques, an amino group can be introduced in the triazine ring by replacement by an appropriately substituted halogeno, mercapto, alkoxy, alkylmercapto or trihalogenomethyl-s-triazine.

As indicated, the present invention also pertains to the physiologically acceptable nontoxic acid addition salts of these basic compounds. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The anti-ulcergenic activity of these compounds can be conveniently observed in recognized laboratory models. For example, in the well known Shay rat, the following are typical values for representative compounds:

Table 1

| X | Y | Anti-ulcer Activity |
|---|---|---|
| $-SCF_3$ | H | 87% |
| $-SCH_3$ | H | 55% |
| $-SO_2CH_3$ | H | 34% |
| $-CF_3$ | Cl | 51% |
| $-CF_3$ | $-O(CH_3)_2OCH_3$ | 41% |
| $-Br$ | $-OCH_3$ | 49% |

Likewise the diuretic activity can be conveniently observed in well known laboratory models, as for example the increase in the urine excretion ratio for saline loaded rats over a period of 5 hours:

Table 2

| X | Y | Ratio of Excretion |
|---|---|---|
| $-SCH_3$ | H | 1.46 |
| $-SO_2CH_3$ | H | 1.24 |
| $-SO_2N(CH_3)_2$ | H | 1.25 |
| $-SO_2NH_2$ | H | 1.52 |

In general, the compounds demonstrate these activities in daily dosage ranges of from about 1 to about 100 mg/kg of body weight. For example, the above values correspond to a response at a dosage range of 20 mg/kg i.p.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

The following examples will further serve to typify the nature of this invention without being a limitation thereof, the invention being defined solely by the appended claims.

EXAMPLE 1

2,4-diamino-6-(3-trifluoromethylthiophenyl)-s-triazine 2.9 g of m-trifluoromethylthiobenzonitrile (b.p. 86°–88° C/40 mm Hg) and 1.4 g of dicyanodiamide are dissolved in 3 ml of methylcellosolve and the mixture is then combined with 0.3 g of caustic potash and refluxed for 5 hours. After cooling, the mixture is diluted with water and extracted with ether, and the extract, after evaporation, is recrystallized from methanol. Melting point of the obtained material: 172°–174° C; yield: 2.4 g.

EXAMPLE 2

2,4-diamino-6-(3-methylthiophenyl)-s-triazine 4.0 g of m-methylthiobenzonitrile, 2.7 g of dicyanodiamide and 2.0 g of caustic potash are dissolved in 20 ml of methyl cellosolve, and the mixture is refluxed for 4 hours. After cooling, the mixture is diluted with water and the separated crystals are recrystallized from dioxane. Melting point: 229°–230° C; Yield: 3.4 g.

EXAMPLE 3

2,4-diamino-6-(3-methylsulfonylphenyl)-s-triazine 5.0 g of m-methylsulfonylbenzonitrile (101°–103° C), 2.8 g of dicyanodiamide and 2.0 g of caustic potash are refluxed in 20 ml of methyl cellosolve for 3 hours. After cooling, the mixture is diluted with water, and the separated crystals are recrystallized from ethanol. Melting point: 228°–289° C; yield: 4.8 g.

EXAMPLE 4

2,4-diamino-6-(3-dimethylsulfamylphenyl)-s-triazine 5.7 g of benzoguanamine is heated in 12 g of chlorosulfonic acid at 130° to 140° C for 4 hours. After cooling, the reaction mixture is added dropwise into a mixture of 40 ml of 40% aqueous dimethylamine and 50 ml of dioxane under agitation and ice cooling, and after one hour agitation, the mixture is evaporated to dryness under vacuum. Thereafter, water is added to the mixture and the separated crystals are filtered out and recrystallized from dioxane. Melting point: 250°–251° C; yield: 8.8 g.

EXAMPLE 5

2,4-diamino-6-(3-sulfamylphenyl)-s-triazine 6.0 g of benzoguanamine is heated in 30 g of chlorosulfonic acid at 130° to 140° C for 4 hours. After cooling, the mixture is added dropwise into 300 ml of 28% aqueous ammonia with stirring and after 1 hour, the insoluble matter is filtered out and recrystallized from aqueous dimethylsulfoxide. Melting point: over 290° C; yield: 2.0 g.

EXAMPLE 6

2,4-diamino-6-(3-trifluoromethyl-6-chlorophenyl)-s-triazine 4.0 g of 3-cyano-4-chlorobenzotrifluoride (90°–102° C/29 mm Hg), 2.0 g of dicyanodiamide and 1.0 g of caustic potash are refluxed in 10 ml of diglyme for 3 hours. After cooling, the mixture is diluted with water and the separated crystals are recrystallized from methanol. Melting point: 210°–212° C; yield: 3.8 g.

EXAMPLE 7

2,4-diamino-6-(3-trifluoromethyl-6-methoxyethoxyphenyl)-s-triazine 6.3 g of 3-cyano-4-chlorobenzotrifluoride, 3.1 g of dicyanodiamide and 1.0 g of caustic potash are refluxed in 10 ml of methyl cellosolve for 5 hours. After cooling, the mixture is diluted with water and the separated crystals are recrystallized from methanol. Melting point: 224°–226° C; yield: 4.3 g.

EXAMPLE 8

2,4-diamino-6-(3-bromo-6-methoxyphenyl)-s-triazine 5.0 g of 2-methoxy-5-bromobenzoic acid methylester (oil) prepared from 5-bromosalicylic acid and 3.0 g of biguanide are refluxed in 50 ml of ethanol with stirring for 8 hours. After cooling, the separated crystals are collected and recrystallized from aqueous dimethylsulfoxide. Melting point: 294°–297° C; yield: 3.2 g.

What is claimed is:

1. A compound selected from the group consisting of a benzoguanamine of the formula:

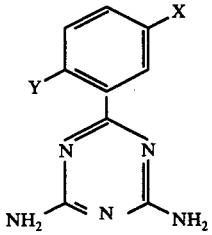

wherein

X is lower alkylthio, lower alkylsulfonyl, sulfamyl, N,N-di(lower alkyl)sulfamyl, trifluoromethyl or trifluoromethylthio; and Y is hydrogen, halogeno, lower alkoxy or lower alkoxy(lower alkoxy), and the pharmaceutically acceptable acid addition salts thereof.

2. A compound according to claim 1 wherein X is methylthio, methylsulfonyl, sulfamyl, dimethylsulfamyl, trifluoromethyl or trifluoromethylthio.

3. A compound according to claim 1 wherein Y is hydrogen, chloro, methoxy or methyoxyethoxy.

4. A compound selected from the group consisting of a benzoguanamine of the formula:

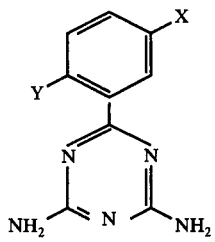

wherein
X is methylthio, methylsulfonyl, sulfamyl, dimethylsulfamyl or trifluoromethylthio; and
Y is hydrogen, chloro, methoxy or methoxyethoxy, and the pharmaceutically acceptable acid addition salts thereof.

5. The compound according to claim 4 which is 2,4-diamino-6-(3-trifluoromethylthiophenyl)-s-triazine.

6. The compound according to claim 4 which is 2,4-diamino-6-(3-methylthiophenyl)-s-triazine.

7. The compound according to claim 4 which is 2,4-diamino-6-(3-methylsulfonylphenyl)-s-triazine.

8. The compound according to claim 4 which is 2,4-diamino-6-(3-dimethylsulfamylphenyl)-s-triazine.

9. The compound according to claim 4 which is 2,4-diamino-6-(3-sulfamylphenyl)-s-triazine.

10. 2,4-Diamino-6-(3-trifluoromethyl-6-chlorophenyl)-s-triazine.

11. The compound according to claim 4 which is 2,4-diamino-6-(3-trifluoromethyl-6-methoxyethoxyphenyl)-s-triazine.

12. The compound according to claim 4 which is 2,4-diamino-6-(3-bromo-6-methoxyphenyl)-s-triazine.

13. The method of achieving an anti-ulcer effect in humans and other animals which comprises administering to a human or animal in need thereof an anti-ulcer effective amount of a compound according to claim 1.

14. A pharmaceutical composition comprising an anti-ulcer effective amount of a compound according to claim 1 in combination with a pharmaceutical carrier.

* * * * *